US 8,556,886 B2

(12) United States Patent
Youssefi

(10) Patent No.: US 8,556,886 B2
(45) Date of Patent: Oct. 15, 2013

(54) COMBINATION OF EXCIMER LASER ABLATION AND FEMTOSECOND LASER TECHNOLOGY

(76) Inventor: Gerhard Youssefi, Landshot (DE)

( * ) Notice: Subject to any disclaimer, the term of this patent is extended or adjusted under 35 U.S.C. 154(b) by 46 days.

(21) Appl. No.: 13/015,979

(22) Filed: Jan. 28, 2011

(65) Prior Publication Data

US 2011/0202045 A1 Aug. 18, 2011

Related U.S. Application Data

(63) Continuation of application No. PCT/EP2009/059068, filed on Jul. 15, 2009.

(30) Foreign Application Priority Data

Aug. 1, 2008 (DE) .......................... 10 2008 035 995

(51) Int. Cl.
*A61B 18/20* (2006.01)
(52) U.S. Cl.
USPC ...................................... 606/5; 606/4; 606/10
(58) Field of Classification Search
USPC .................. 606/4–6, 10–12; 351/200, 246
See application file for complete search history.

(56) References Cited

U.S. PATENT DOCUMENTS

| 5,425,727 A | 6/1995 | Koziol |
| 5,777,719 A | 7/1998 | Williams |
| 5,891,132 A | 4/1999 | Hohla |
| 5,928,221 A | 7/1999 | Sasnett |
| 5,949,521 A | 9/1999 | Williams |
| 5,984,916 A | 11/1999 | Lai |
| 6,033,075 A | 3/2000 | Fujieda |
| 6,086,204 A | 7/2000 | Magnante |
| 6,090,100 A | 7/2000 | Hohla |
| 6,095,651 A | 8/2000 | Williams |
| 6,132,424 A | 10/2000 | Tang |
| 6,159,205 A | 12/2000 | Woodward et al. |
| 6,271,936 B1 | 8/2001 | Yu et al. |
| 6,322,216 B1 | 11/2001 | Yee |
| 6,325,702 B2 | 12/2001 | Robinson |
| 6,394,999 B1 | 5/2002 | Williams |

(Continued)

FOREIGN PATENT DOCUMENTS

| DE | 19727573 | 5/1998 |
| DE | 20 2005 018911 | 3/2006 |

(Continued)

OTHER PUBLICATIONS

PCT International Search Report regarding U.S. Appl. No. 13/015,979; International Application No. PCT/EP2009/059068; International Filing Date: Jul. 15, 2009; Priority Date: Aug. 1, 2008 for Applicant Technolas Perfect Vision GmbH.

(Continued)

*Primary Examiner* — Ahmed Farah
(74) *Attorney, Agent, or Firm* — Akin Gump Strauss Hauer & Feld LLP

(57) ABSTRACT

The invention relates to an apparatus and a method for providing data for vision correction utilizing a volumetric ablation and an intrastromal manipulation. The provided data may be used by a laser ablating the surface of the cornea in combination with a laser which operates intrastromal to optimize a corneal re-shaping procedure. One aspects of the invention relates to the minimization of the amount of corneal tissue to be removed.

17 Claims, 8 Drawing Sheets

(56) References Cited

U.S. PATENT DOCUMENTS

| | | |
|---|---|---|
| 6,413,251 B1 | 7/2002 | Williams |
| 6,454,761 B1 | 9/2002 | Freedman |
| 6,500,171 B1 | 12/2002 | Williams |
| 6,508,812 B1 | 1/2003 | Williams |
| 6,511,180 B2 | 1/2003 | Guirao et al. |
| 6,607,521 B2 | 8/2003 | Vinciguerra |
| 6,635,051 B1 | 10/2003 | Hohla |
| 6,715,877 B2 | 4/2004 | Molebny |
| 6,755,819 B1 | 6/2004 | Waelti |
| 6,808,266 B2 | 10/2004 | Youssefi et al. |
| 6,848,790 B1 | 2/2005 | Dick |
| 6,923,802 B2 | 8/2005 | Williams |
| 6,997,555 B2 | 2/2006 | Dick |
| 7,380,942 B2 | 6/2008 | Molebny |
| 2002/0026180 A1 | 2/2002 | Nakamura |
| 2002/0075451 A1 | 6/2002 | Ruiz |
| 2002/0082629 A1 | 6/2002 | Cox |
| 2003/0023233 A1 | 1/2003 | Smith et al. |
| 2003/0048413 A1 | 3/2003 | Ross |
| 2003/0128335 A1 | 7/2003 | Campin |
| 2003/0193647 A1 | 10/2003 | Neal |
| 2004/0002697 A1 | 1/2004 | Youssefi et al. |
| 2004/0021874 A1 | 2/2004 | Shimmick |
| 2005/0149005 A1* | 7/2005 | Bille .............................. 606/5 |
| 2005/0159733 A1 | 7/2005 | Dick |
| 2005/0273088 A1 | 12/2005 | Youssefi et al. |
| 2006/0206102 A1* | 9/2006 | Shimmick ..................... 606/4 |
| 2008/0033408 A1 | 2/2008 | Bueler |
| 2008/0058780 A1 | 3/2008 | Vogler |

FOREIGN PATENT DOCUMENTS

| | | |
|---|---|---|
| DE | 10 2005 006897 | 8/2006 |
| EP | 0697611 | 2/1996 |
| EP | 1396244 A2 | 3/2004 |
| EP | 1719483 | 11/2006 |
| JP | 2000300596 | 10/2000 |
| JP | 2002524144 | 8/2002 |
| WO | 9527535 | 10/1995 |
| WO | 9611655 | 4/1996 |
| WO | 9848746 | 11/1998 |
| WO | 2004095187 | 7/2000 |
| WO | 0124688 | 4/2001 |
| WO | 0128410 A | 4/2001 |
| WO | 0128477 A1 | 4/2001 |
| WO | 0234178 | 5/2002 |
| WO | 03068103 | 8/2003 |
| WO | 03075778 | 9/2003 |
| WO | 2004041104 | 5/2004 |
| WO | 2004052253 A1 | 6/2004 |
| WO | 2004053568 | 6/2004 |
| WO | 2005007002 | 1/2005 |
| WO | 2007012924 | 2/2007 |
| WO | 2007143111 | 12/2007 |

OTHER PUBLICATIONS

Damien Gatinel, et al., "Three-dimensional representation and qualitative comparisons of the amount of tissue ablation to treat mixed and compound astigmatism," Journal of Cataract and Refractive Surgery, vol. 28 (No. 11), p. 2026-2034 (Nov. 1, 2002).
US 5,423,802, 06/1995, Marshall (withdrawn)

* cited by examiner

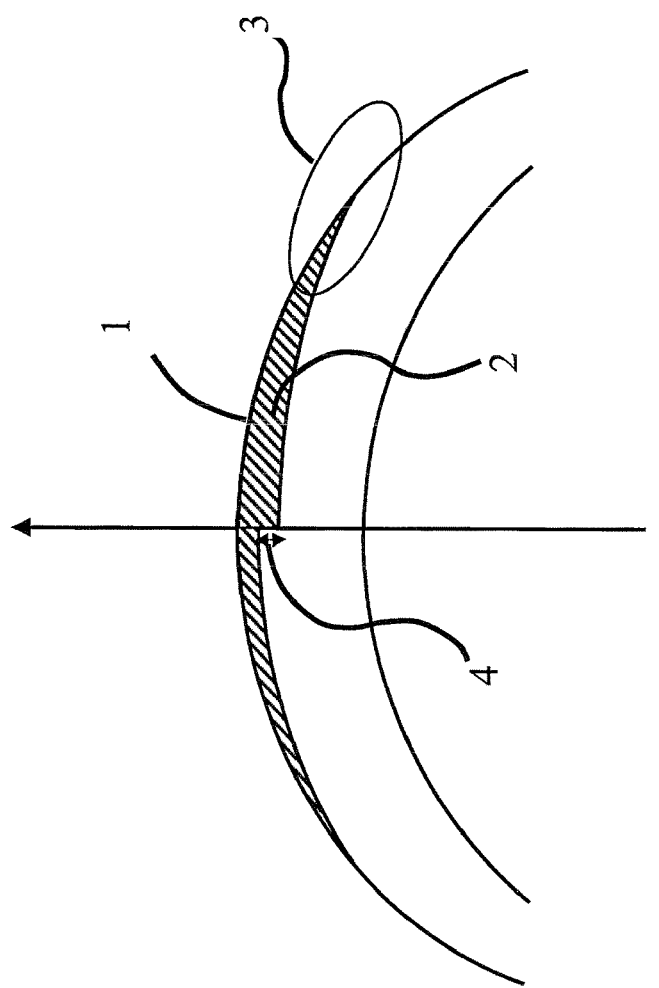

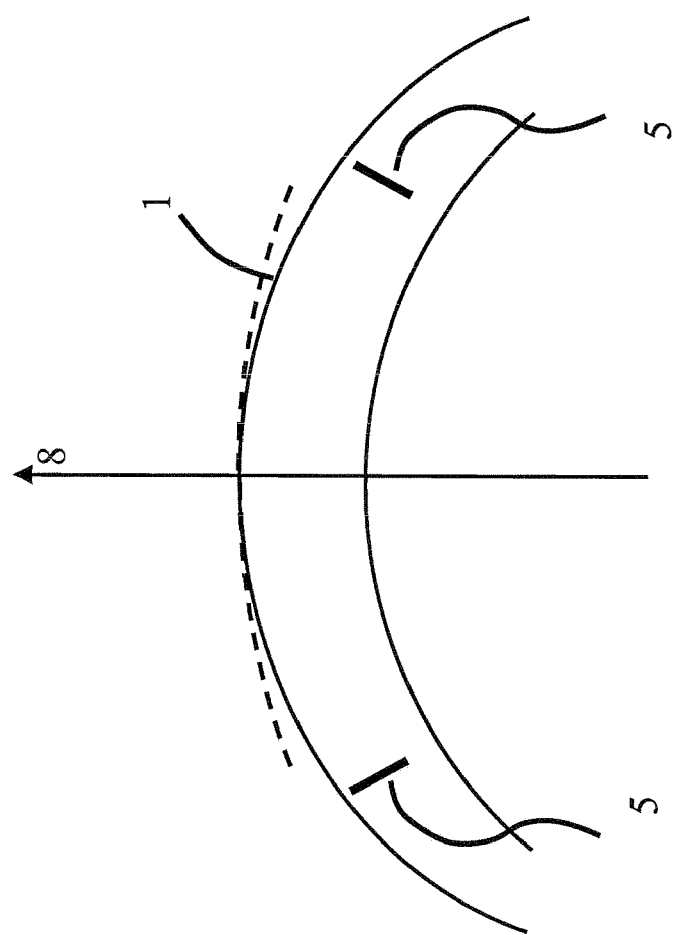

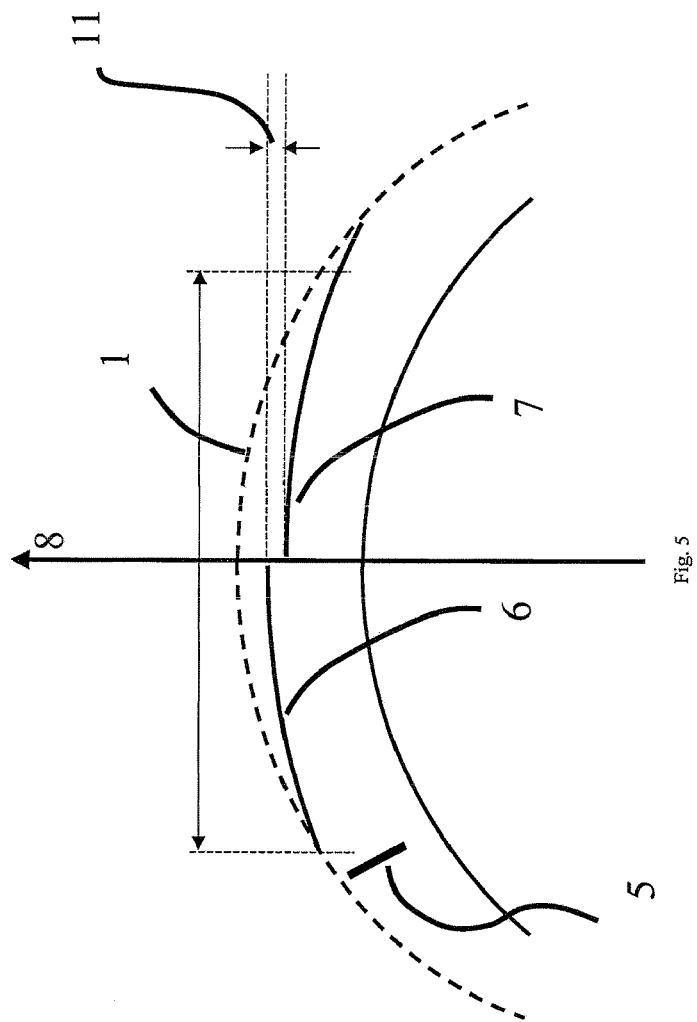

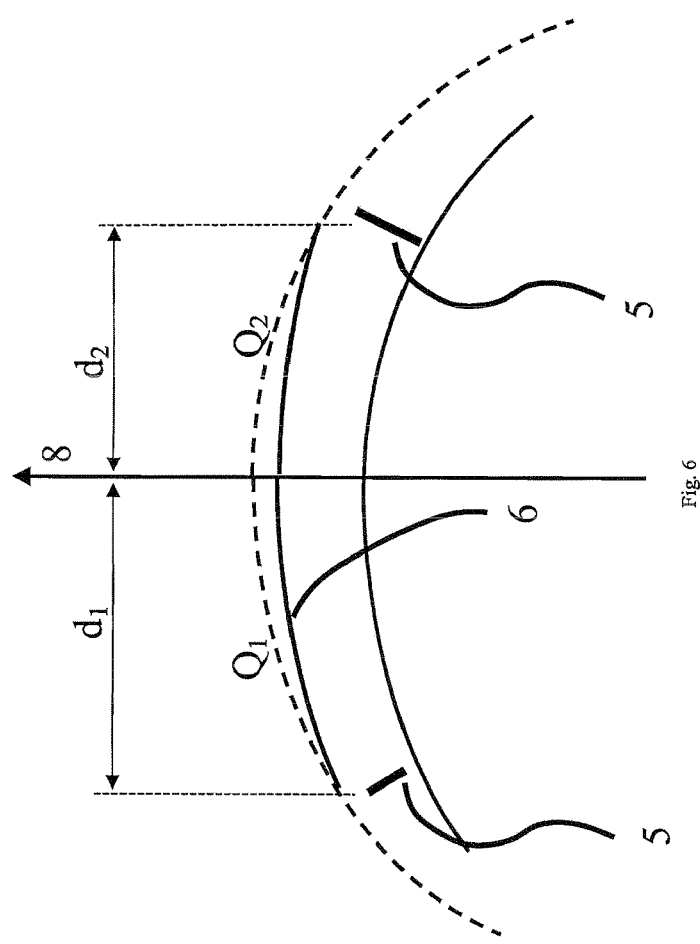

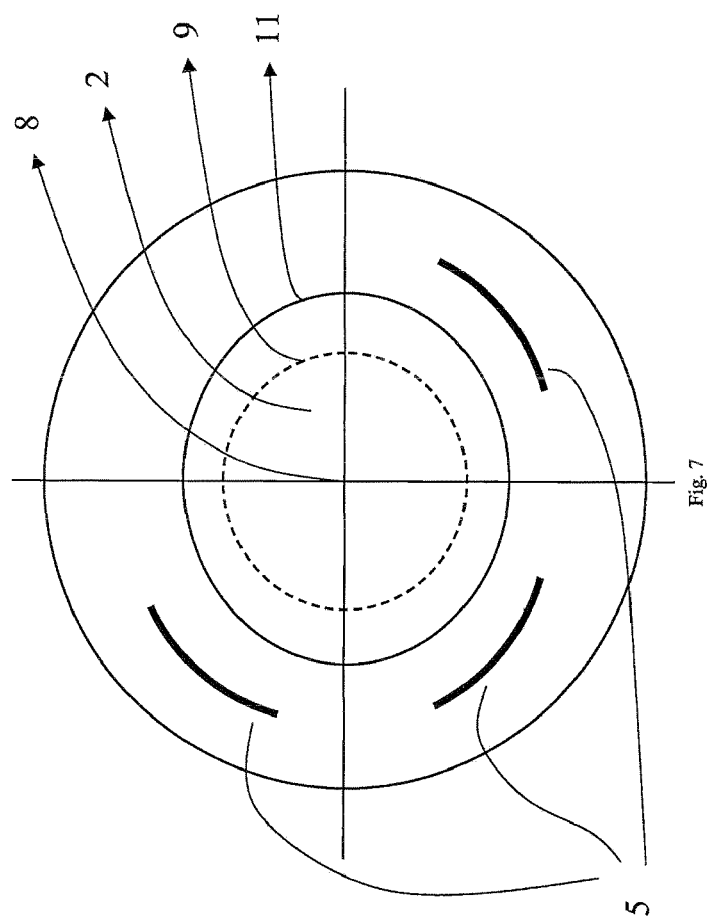

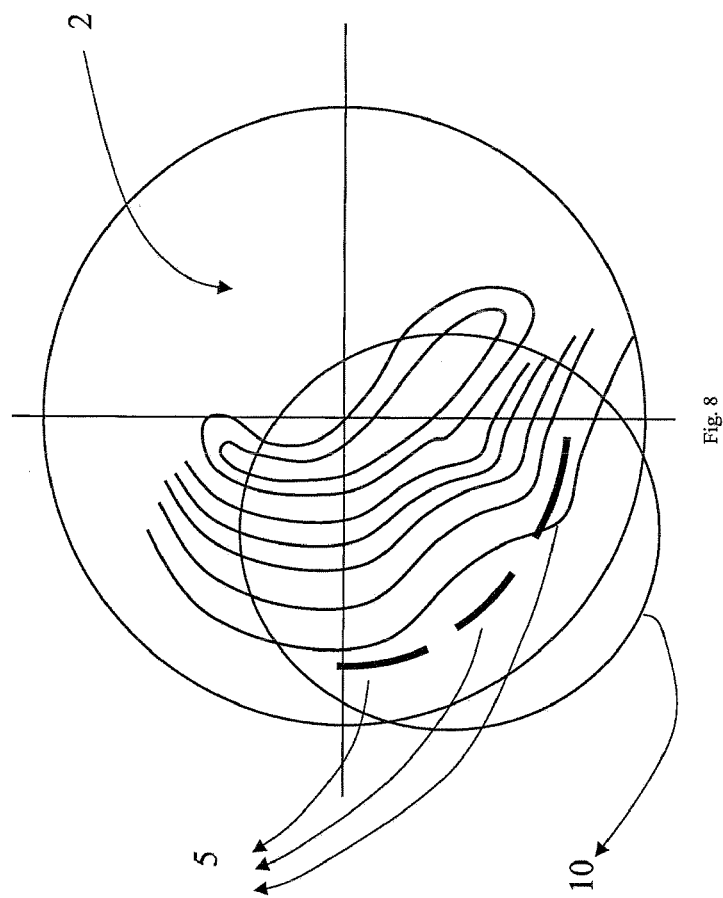

COMBINATION OF EXCIMER LASER ABLATION AND FEMTOSECOND LASER TECHNOLOGY

This is a continuation of International Application PCT/EP2009/059068, with an international filing date of Jul. 15, 2009, and which claims the benefit of German Application No. 10 2008 035 995.5, with a foreign filing date of Aug. 1, 2008.

FIELD OF INVENTION

The invention relates to an apparatus and a method for providing data for vision correction utilizing a volumetric ablation and an intrastromal manipulation. The provided data may be used by an excimer laser for ablating the surface of the cornea in combination with a femtosecond laser which operates intrastromal to optimize a corneal re-shaping procedure.

BACKGROUND OF THE INVENTION

Known procedures for vision correction like PRK, LASIK, and LASEK are typically used to correct myopic and hyperopic vision errors with or without astigmatism by utilizing a volumetric ablation. In customized treatments also higher order aberrations of the eye can be addressed.

The applicability of known treatment procedures depends on certain parameters, e.g., the corneal thickness of an eye. That is, in case the remaining corneal thickness after applying one of the above vision correction treatments is below a required minimum thickness the eye cannot be corrected in this way. Due to such exclusion criteria, not all potentially correctable eye aberrations can actually be corrected by the application of the above vision correction procedures.

Also, known laser correction treatments may cause an unintended biodynamic effect in the cornea and consequently affect the vision error correction, i.e., the biodynamic effect deteriorates the accuracy of the treatment As an example, to correct a myopic vision error corneal tissue is removed from a central portion of the eye to flatten the cornea. The biodynamic effect of the cornea caused by this treatment may lead to an induced spherical aberration. Therefore, additional corneal tissue has to be ablated to correct the induced error.

According to WO-A-2004/002382, from Technolas GmbH, a method for providing a LASIK or LASEK myopia correction comprises a controlled biodynamic ablation. An ablation ring outside of the optical zone produces a biodynamic flattening of the central region of the cornea which, in turn reduces the ablation depth of corneal tissue in the optical zone to effect a myopia correction.

SUMMARY

An aspect of the invention is to provide an improved method and apparatus for optimizing a vision correction procedure and to provide a laser treatment system using said method and/or apparatus. Another aspect of the invention is to improve the applicability of laser vision correction.

The above objects are achieved by the features of the claims. Aspects of the invention are directed to a method and an apparatus for providing data for vision correction as well as a laser treatment system using the data for vision correction. The concept of the present invention is based on the combination of a volumetric ablation, e.g. by an excimer laser, and at least one intrastromal manipulation, e.g. by a femtosecond laser, which avoids or induces a corneal biodynamic shape change to optimize a vision correction treatment. In an aspect of the invention the volumetric ablation can be minimized, i.e., less corneal tissue has to be ablated to correct a detected vision error.

Input data for the method/apparatus according to the present invention may be diagnostic data, preferably at least one of a subjective refractive error and a measured refractive error. The measured refractive error may be obtained by at least one of a wavefront sensor, topographical measurement device or a pachymetry measurement device. Low order aberrations, typically understood as being for example the $2^{nd}$ order Zernike type aberrations expressed in sphere, cylinder and related axis, may be determined by a subjective refractive error, e.g. considering the verbal feedback of a patient. High order aberrations typically understood to be for example $3^{rd}$ and higher order Zernike type aberrations such as coma and trefoil ($3^{rd}$ order) and spherical aberration and secondary astigmatism ($4^{th}$ order), may be determined by measurement means and/or by mathematically given shape change parameters. The mathematically given shape change parameters may represent unintentional vision errors which are induced by a vision correction treatment, such as an induced spherical aberration by an excimer laser ablation process.

The calculation of the intrastromal manipulation may basically depend on the one hand on data representative of the corneal topography and/or pachymetry data which may be classified together as the corneal architecture and on the other hand on the intended type of correction, e.g., myopic (flattening) or hyperopic (steepening). In this context the three-dimensional diagnostic data can be used to determine parameters, e.g. the location and the amplitude of an intrastromal manipulation. Data representative of the all over corneal structure can be used to determine the locations of an intrastromal manipulation.

The output data of the method/apparatus according to the present invention may be used to control a laser treatment system for performing a laser vision correction treatment. The output data may also be in a form from which the treatment pattern can be calculated in order to be able to control a laser treatment system.

According to an aspect of the invention low order aberrations are basically corrected by a volumetric ablation, e.g. by an excimer laser, and high order aberrations are basically corrected by at least one intrastromal manipulation, e.g. by a femtosecond laser. In addition, the volumetric ablation can be minimized by the application of an intrastromal manipulation. An intrastromal manipulation may be in form of a disruption or a cut within the corneal structure. This intrastromal manipulation may avoid or induce a bio-dynamic shape change of the cornea. In order to optimize the data for a vision correction treatment the volumetric ablation profile(s) and the intrastromal manipulation(s) may be determined and/or altered iteratively.

It is noted that according to the invention also other small scale modifications to a corneal profile can be determined such as data for generating multifocal corneas to reverse presbyopia. For performing such a correction an intrastromal manipulation may be applied after the application of a volumetric ablation, which is used to remove the refractive error.

The combined scheme of volumetric ablation and intrastromal manipulation may be even more dominant in the case of highly aberrated eyes, in which an intrastromal manipulation may cover the majority of the corneal manipulation due to significant aberrations and related mechanical deformations of a cornea.

According to an aspect of the invention at least one volumetric ablation profile and at least one intrastromal manipulation is calculated based on diagnostic data representing a refractive error of a cornea of an eye. At least one volumetric ablation profile and at least one intrastromal manipulation is selected to optimize the combined treatment of a volumetric ablation and an intrastromal manipulation to correct said refractive error.

According to a further aspect of the invention the volumetric ablation profile(s) and the intrastromal manipulation(s) are optimized such that the amount of corneal tissue to be ablated by volumetric ablation is minimized.

BRIEF DESCRIPTION OF THE DRAWINGS

Illustrative, non-limiting embodiments of the present invention will be described by way of example with reference to the accompanying drawings, in which the same reference number is used to designate the same or similar components in different figures, and in which:

FIG. 3 is a schematic sectional view of the surface of a cornea showing the volumetric ablation with and without a compensation of an induced spherical aberration by an additional volumetric ablation;

FIG. 4 is a schematic sectional view of a cornea with an intrastromal manipulation according to the invention;

FIG. 5 is a schematic illustration of a cornea with both a volumetric ablation and an intrastromal manipulation according to the invention;

FIG. 6 is a schematic sectional view of a cornea with an intrastromal manipulation asymmetrically with respect to the optical axis of an eye to be treated according to the invention;

FIG. 7 is a schematic front view of a first cornea with both a volumetric ablation and an intrastromal manipulation according to the invention;

FIG. 8 is a schematic front view of a second cornea with both a volumetric ablation and an intrastromal manipulation according to the invention;

DETAILED DESCRIPTION

Figure 1:
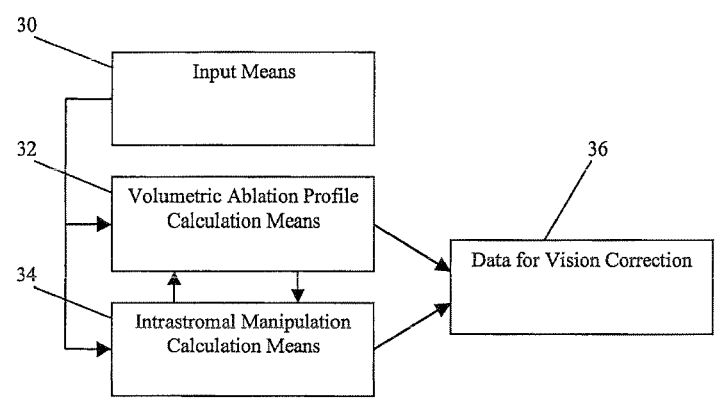
FIG. 1 is a block diagram of an apparatus for providing data for vision correction according to the invention.

FIG. 1 shows a block diagram of an apparatus for providing data for vision correction 36 utilizing a volumetric ablation 2 and an intrastromal manipulation 5 according to the invention. It is noted that the corresponding method of the invention works in the way in which the apparatus is described. The apparatus comprises an input means for receiving diagnostic data representing a refractive error of an eye. The data may relate to at least one of subjective data, topographic data, wavefront data, and pachymetry data. The diagnostic data may be provided directly by a respective measurement device. Alternatively, a storage device (not shown) can be used for storing diagnostic data. Also, a combination of stored data with directly measured/determined data can be used to provide data for vision correction 36 according to the invention.

A volumetric ablation profile calculation means 32 calculates based on the diagnostic data, e.g. received by input means 30 or from the memory, at least one volumetric ablation profile which may be utilized to control an adequate laser device, such as an excimer laser. The volumetric ablation profile is calculated with reference to an optical zone for the eye to be treated. The optical zone preferably covers the area of the dark adapted pupil 9 (mesopic pupil).

An intrastromal manipulation calculation means 34 calculates based on the diagnostic data, e.g. received by an input means 30 or from the memory, at least one intrastromal manipulation 5 which may be utilized to control an adequate laser device, such as a femtosecond laser. The intrastromal manipulation 5 can be calculated to be located outside the dark adapted pupil 9 and can comprise the determination of at least one of the location, length, width, and depth of the intrastromal manipulation. The intrastromal manipulation 5 can be a disruption or a cut within the corneal structure. The intrastromal manipulation 5 at least compensates for an unintended aberration induced by the volumetric ablation, e.g., it corrects an induced spherical aberration caused by ablating corneal tissue in the center portion of a cornea when correcting for example a myopic vision error.

As illustrated by arrows the volumetric ablation profile calculation means 32 and the intrastromal manipulation calculation means 34 may be connected to each other to exchange data. The processing may be started from the volumetric ablation profile calculation means 32 or the intrastromal manipulation calculation means 34 or even concurrently. Calculated data may be communicated to the other calculation means for an optimization. The data may be optimized in an iterative manner.

Further, at least one of each of the calculated volumetric ablation profile and the intrastromal manipulation is selected to optimize the vision correction treatment. The calculation leads to an optimum combination of the volumetric ablation (s) 2 and the intrastromal manipulation(s) 5. In one aspect of the invention the optimization is executed regarding a determined total vision correction and/or regarding the minimization of the amount of corneal tissue to be ablated by volumetric ablation.

In an exemplary embodiment of such a calculation procedure the $2^{nd}$ order Zernike aberrations (defocus and astigmatism) or the subjective refractive error expressed in sphere, cylinder and axis may be used to determine the major volumetric tissue removal based on, e.g., a thin lens formula or a wavefront guided ablation algorithm. The depth of the ablation which is a direct result of the amplitude of the correction (expressed by the spherical equivalent e.g. sphere+½ astigmatism) and the optical zone is then used to predict the amount of the induced spherical aberration. Mathematical models show that the deeper the ablation is or in other words the more tissue has been removed, the more spherical aberration will be induced. Also the preoperatively existing spherical aberration or corneal asphericity may be used to evaluate the amount of total spherical aberration to be corrected. In a next step the amount of the surgically induced spherical aberration (expressed in μm of a specific Zernike amplitude) for the given optical zone will be used to determine the position and the depth of the intrastromal manipulation. Such an intrastromal manipulation may be expressed in the radial distance, meridial length and the depth of the application.

Figure 2:
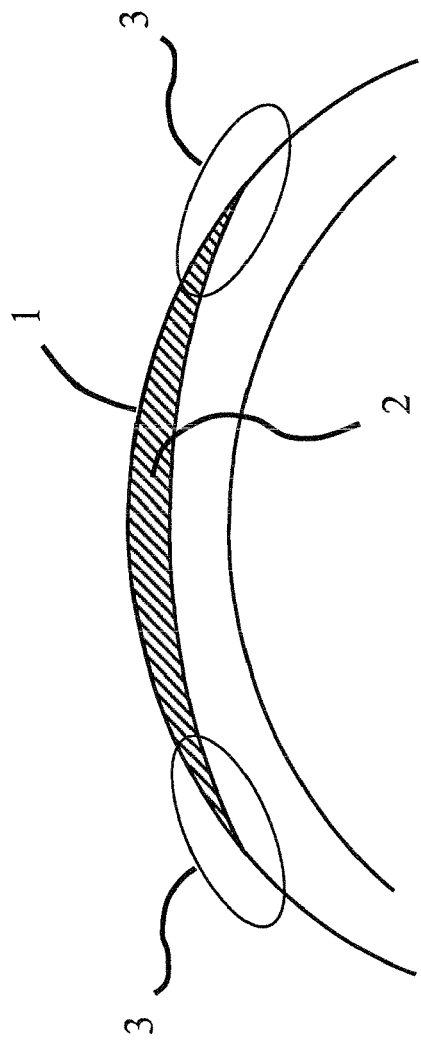
FIG. 2 is a schematic sectional view of a cornea with a volumetric ablation and an induced spherical aberration.

FIG. 2 illustrates a sectional view of a cornea. The preoperative corneal surface 1 of the eye to be treated is ablated by volumetric ablation 2 in a central part of the cornea to compensate for a myopic vision error. The volumetric ablation 2 leads in the presented example to a flattened postoperative corneal surface. With a volumetric removal of corneal tissue a bio-dynamic response may be caused which leads to an unintended induced spherical aberration within a region 3 encircled in FIG. 2. This region 3 is present along the outer circumference of the ablated cornea. This bio-dynamic response is due to the physical characteristics of the corneal tissue and the structure of the eye.

FIG. 3 schematically illustrates the additional amount of volumetric ablation 2 needed to compensate for an unintended induced spherical aberration as shown in FIG. 2 to attain an intended shape of the corneal surface. In particular, the left part of FIG. 3 corresponds to the corneal surface as shown in FIG. 2, illustrating a pre-operative corneal surface 1, a post-operative corneal surface resulting from a volumetric ablation 2 and an unintentional induced spherical aberration. The right part of FIG. 3 shows a corrected post-operative corneal surface, which results from an additional volumetric ablation 4. The additional volumetric ablation 4 of corneal tissue is necessary to compensate for said surgically induced spherical aberration.

FIG. 4 shows a sectional view of a cornea with intrastromal manipulations 5. Intrastromal manipulations 5 can be provided in the periphery outside of the dark adapted pupil 9 of an eye, e.g. by a femtosecond laser. Intrastromal manipulations 5 influence the corneal shape and can support the re-shaping process of the anterior corneal surface. According to FIG. 4, the intrastromal manipulations 5 lead to a flattening of the corneal surface in the central part of the cornea as illustrated by the dashed line. An intrastromal manipulation may be applied symmetrically with respect to the optical axis 8 of the eye to be treated as shown in FIG. 4, but also in an asymmetric way as will be discussed, i.a., with reference to FIGS. 6 and 8. In FIG. 4 the treatment axis coincides with the optical axis 8 of the pupil of the eye.

FIG. 5 illustrates a sectional view of a cornea with both options to apply the correction, i.e., volumetric ablation with and without intrastromal manipulation. The right side shows the effect of a procedure which utilized only volumetric tissue removal using an excimer laser while the left side shows the effect of the combination of an intrastromal manipulations 5 and a volumetric ablation. The shape of the cornea has been changed from the preoperative shape 1 into the same curved surface 6 and 7. While the shape of the curves are same, i.e. they have the same refractive effect, the surface of the cornea 7 created by only volumetric ablation is positioned much deeper than the surface 6 of the cornea generated by the combination of both effects. The additional ablation depth needed for an excimer based application only is shown as volumetric ablation difference 11. As a result of the application of the intrastromal manipulations 5 less volumetric ablation may be necessary to obtain a flattened corneal surface.

FIG. 6 shows a schematic sectional view of a cornea with intrastromal manipulations 5 which are asymmetrically with respect to the optical axis 8 of the eye to be treated. In case of a known asymmetry in the mechanical corneal shape, an adjusted intrastromal manipulation 5 can be used. One way of such an adjustment is to adjust the distance of the intrastromal manipulations 5 from the optical axis 8 according to the corneal construction. As exemplarily shown in FIG. 6, the left intrastromal manipulation 5 is applied at a distance $d_1$ from the optical axis 8 of the eye to be treated. The right intrastromal manipulation 5 is applied at a distance $d_2$ from said optical axis 8, wherein $d_2 < d_1$.

Typical cases for such adjustments may be different gradients in the asphericity parameter Q or even higher levels of irregularity in the corneal shape. FIG. 6 illustrates an asphericity parameter $Q_1$ and $Q_2$ providing a measure for the aspheric property of the surface of the eye in the section within distance $d_1$ and $d_2$, respectively. Also, high order aberrations such as significant coma may be addressed by an adjusted application scheme of the intrastromal manipulation 5. The determination of the intrastromal manipulation 5 is not limited to irregular anterior surfaces only and may include other information, e.g., a pachymetry profile of the examined cornea.

FIG. 7 shows a front view of a first cornea. The volumetric ablation 2 is applied in a central part of the cornea within the treatment area 11. As illustrated, the treatment area 11 of the volumetric ablation may be greater than the dark adapted pupil 9 of the eye. This is advantageous in order to avoid vision defects in dark light conditions, wherein the pupil diameter reaches its maximum and the border of a volumetric ablation 2 may affect vision. Further, intrastromal manipulations 5 may be applied in the periphery outside of the dark adapted pupil 9 for optimizing the overall treatment in view of the correction result and to minimize the amount of volumetric ablation 2. In this case three intrastromal manipulations are shown which are applied outside of the treatment area 11 substantially along a circumference about the optical axis 8. More specifically the intrastromal manipulations are sections of a curve arranged at a distance to and following the outer periphery of the treatment 30 area 11. The intrastromal manipulations are arranged at irregular distances from each other along said curve. Thus, this arrangement is made in an asymmetric manner in order to compensate for a respective irregular shape of the cornea.

FIG. 8 shows a front view of a second cornea, wherein the intrastromal manipulation 5 at least partially corrects an irregular region 10 of the cornea. The intrastromal manipulation 5 is provided in the left lower portion of the cornea substantially along a circumference about the optical axis 8 to compensate for the irregular region 10, which is also located in the left 5 portion of the cornea. In addition, a volumetric ablation 2 is applied to finalize the treatment, i.e., to correct a remaining aberration.

While certain embodiments have been chosen to illustrate the invention it will be understood by those skilled in the art that changes and modifications can be made therein without departing from the scope of the invention as defined in the appended claims. In particular it is noted that even though exemplary reference was made to an myopic vision error also other vision errors will benefit from the present invention.

The invention claimed is:

1. A system for providing data for vision correction utilizing a volumetric ablation and an intrastromal manipulation, comprising:
    first computer software receiving diagnostic data representing a refractive error of a cornea of an eye;
    second computer software calculating at least one volumetric ablation profile based on said diagnostic data;
    third computer software calculating at least one intrastromal manipulation based on said diagnostic data;
    fourth computer software selecting at least one volumetric ablation profile and at least one intrastromal manipulation to optimize a combined treatment of a volumetric ablation and an intrastromal manipulation to correct said refractive error;
    wherein the intrastromal manipulation causes a bio-dynamic shape change of at least a portion of the cornea.

2. The system of claim 1, wherein the combined treatment is optimized by selecting a specific ablation profile and a corresponding intrastromal manipulation such that the amount of corneal tissue to be ablated by volumetric ablation is minimized.

3. The system of claim 1, wherein the combined treatment is optimized such that the intrastromal manipulation is selected based on a given set of desired corrections.

4. The system of claim 1, wherein the intrastromal manipulations at least partially flattens the cornea.

5. The system of claim 1, wherein the volumetric ablation compensates for low order aberrations, preferably up to the second order.

6. The system of claim 1, wherein the intrastromal manipulations compensates for high order aberrations, preferably from the third order.

7. The system of claim 1, wherein the intrastromal manipulation is a disruption.

8. The system of claim 1, wherein the intrastromal manipulation is formed with a femtosecond laser.

9. The system of claim 1, wherein calculating said at least one intrastromal manipulation comprises determining the location and/or length, width and depth of the manipulation.

10. The system of claim 1, wherein at least one of the intrastromal manipulations is located outside the dark adapted pupil.

11. The system of claim 1, wherein the volumetric ablation is located at least partially within the dark adapted pupil.

12. The system of claim 1, wherein the at least one intrastromal manipulation at least compensates for induced refractive errors caused by the volumetric ablation.

13. The system of claim 1, wherein the diagnostic data comprises a refractive error obtained by subjective patient information and/or a wavefront measurement and/or a topographic measurement.

14. The system of claim 1, wherein the volumetric ablation is an excimer laser ablation.

15. The system of claim 1, further comprising fifth computer software controlling a laser apparatus responsive to the provided data for vision correction.

16. The system of claim 1, further comprising fifth computer software controlling an excimer laser responsive to the calculated volumetric ablation profile and controlling a femtosecond laser responsive to the at least one calculated intrastromal manipulation.

17. The system of claim 1, further comprising a laser treatment system with an excimer laser, and a femtosecond laser.

\* \* \* \* \*